(12) United States Patent
Habeck et al.

(10) Patent No.: US 6,210,657 B1
(45) Date of Patent: *Apr. 3, 2001

(54) USE OF ISOINDOLINONE DERIVATIVES AS STABILIZERS FOR ORGANIC MATERIALS

(75) Inventors: Thorsten Habeck, Meckenheim; Sylke Haremza, Neckargemünd; Hubert Trauth, Dudenhofen; Volker Schehlmann, Römerberg; Horst Westenfelder, Neustadt, all of (DE)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/207,624

(22) Filed: Dec. 9, 1998

(30) Foreign Application Priority Data

Dec. 19, 1997 (DE) ............................... 197 56 778

(51) Int. Cl.[7] ............................ A61K 7/42; A61K 7/44; A61K 7/06; A61K 7/05
(52) U.S. Cl. .......................... 424/59; 424/60; 424/70.9; 424/401; 514/844; 514/970; 514/972
(58) Field of Search ............... 424/401, 59, 60, 424/70.9; 574/844, 970, 972

(56) References Cited

U.S. PATENT DOCUMENTS

| | | | |
|---|---|---|---|
| 4,853,471 | 8/1989 | Rody et al. | 548/261 |
| 5,250,592 | * 10/1993 | Nesvadba | 524/89 |
| 5,858,381 | * 1/1999 | Le Bras et al. | 424/401 |

FOREIGN PATENT DOCUMENTS

| | | |
|---|---|---|
| 1770439 | 5/1968 | (DE) . |
| 57 160 | 8/1982 | (EP) . |
| 1 258 351 | * 12/1971 | (GB) . |
| 1258351 | 12/1971 | (GB) . |

OTHER PUBLICATIONS

Chem. Ber. 100, 2261–2273 (1967) Kranz.

* cited by examiner

Primary Examiner—Jose' G. Dees
Assistant Examiner—Marina Lamm
(74) Attorney, Agent, or Firm—Keil & Weinkauf

(57) ABSTRACT

Isoindolinone derivatives of the formula I,

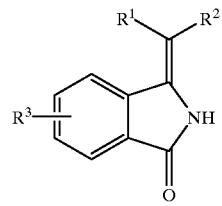

in which the variables have the following meanings:

$R^1$ is hydrogen, $COOR^4$, $COR^4$, $CONR^4R^5$, CN, $C_1$–$C_{20}$-alkyl, $C_2$–$C_{10}$-alkenyl, $C_3$–$C_{10}$-cycloalkyl, $C_3$–$C_{10}$-cycloalkenyl, aryl or heteroaryl, substituted or unsubstituted;

$R^1$ and $R^2$ together are $C_7$–$C_{10}$-bicycloalkyl or $C_7$–$C_{10}$-bicycloalkenyl;

$R^3$ is hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl or heteroaryl, substituted or unsubstituted, substituents which confer solubility in water, selected from the group consisting of carboxylate, sulfonate or ammonium radicals;

$R^4$ and $R^5$ independently of one another are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl; aryl or heteroaryl, substituted or unsubstituted;

are used as stabilizers for organic materials.

4 Claims, No Drawings

USE OF ISOINDOLINONE DERIVATIVES AS STABILIZERS FOR ORGANIC MATERIALS

The invention relates to the use of isoindolinone derivatives as stabilizers for organic materials.

As is known, organic material, in particular plastics and surface coatings, is destroyed very rapidly, especially by the effect of light. This destruction usually becomes apparent by the material yellowing, discoloring, cracking or becoming brittle. The stabilizers and light protection agents used to date have been unable to achieve satisfactory protection against the destruction of organic material by light, oxygen and heat.

Thus, for example, EP-A-057 160 recommends o-hydroxyphenylbenzotriazole derivatives of the formula

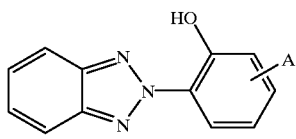

in which A is, for example, polyethyleneoxycarbonylalkyl radicals or polyethyleneoxycarbonylalkylene bridge members connecting two o-hydroxyphenylbenzotriazole systems, as UV absorbers for plastics and surface coatings. Although said o-hydroxyphenylbenzotriazole derivatives have the desired spectroscopic properties (strong absorption bands in the range from 280 to 360 nm), they do not satisfy today's requirements as regards their stabilization and light protection action.

It is an object of the present invention to provide stabilizers and light protection agents which effectively protect organic material.

We have found that this object is achieved according to the invention by the use of isoindolinone derivatives of the formula I,

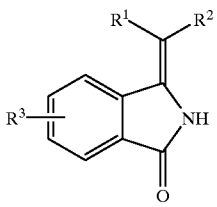

in which the variables independently of one another have the following meanings:

$R^1$ is hydrogen, $COOR^4$, $COR^4$, $CONR^4R^5$, CN, $C_1$–$C_{20}$-alkyl, $C_2$–$C_{10}$-alkenyl, $C_3$–$C_{10}$-cycloalkyl, $C_3$–$C_{10}$-cycloalkenyl, aryl or heteroaryl, substituted or unsubstituted;

$R^2$ is $COOR^4$, $COR^4$, $CONR^4R^5$ or CN;

$R^1$ and $R^2$ together are $C_7$–$C_{10}$-bicycloalkyl or $C_7$–$C_{10}$-bicycloalkenyl;

$R^3$ is hydrogen, $C_1$–$C_{20}$-alkyl, $C_2$–$C_{10}$-alkenyl, $C_3$–$C_{10}$-cycloalkyl, $C_3$–$C_{10}$-cycloalkenyl, $C_1$–$C_{12}$-alkoxy, $C_1$–$C_{20}$-alkoxycarbonyl, $C_1$–$C_{12}$-alkylamino, $C_1$–$C_{12}$-dialkylamino, aryl or heteroaryl, substituted or unsubstituted, substituents which confer solubility in water, selected from the group consisting of carboxylate, sulfonate or alkylammonium radicals;

$R^4$ and $R^5$ independently of one another are hydrogen, $C_1$–$C_{20}$-alkyl, $C_2$–$C_{10}$-alkenyl, $C_3$–$C_{10}$-cycloalkyl, $C_3$–$C_{10}$-cycloalkenyl; aryl or heteroaryl, substituted or unsubstituted;

as stabilizers for organic materials.

Alkyl radicals $R^1$ and $R^3$ to $R^5$ which may be mentioned are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimetliylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethylhexyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals $R^1$ and $R^3$ to $R^5$ which may be mentioned are branched or unbranched $C_2$–$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Cycloalkyl radicals $R^1$ and $R^3$ to $R^5$ which may be mentioned are, preferably, branched or unbranched $C_3$–$C_{10}$-cycloalkyl radicals, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl.

Cycloalkenyl radicals $R^1$ and $R^3$ to $R^5$ which may be mentioned are, preferably, branched or unbranched $C_3$–$C_{10}$-cycloalkenyl radicals having one or more double bonds, such as cyclopropenyl, cyclobutenyl, cyclopentenyl, cyclopentadienyl, cyclohexenyl, 1,3-cyclohexadienyl, 1,4-cyclohexadienyl, cycloheptenyl, cycloheptatrienyl, cyclooctenyl, 1,5-cyclooctadienyl, cyclooctatetraenyl, cyclononenyl or cyclodecenyl.

The cycloalkenyl and cycloalkyl radicals may be unsubstituted or substituted by one or more, e.g. one to three, radicals, such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or may contain from 1 to 3 heteroatoms, such as sulfur or nitrogen, whose free valences may be saturated by hydrogen or $C_1$–$C_4$-alkyl, or oxygen in the ring.

Bicycloalkyl or bicycloalkenyl radicals, which may be formed by $R^1$ and $R^2$ together, which may be mentioned are saturated or unsaturated $C_7$–$C_{10}$ bicyclic ring systems, in particular bicyclic terpenes; such as pinane, pinene, bornane, camphor derivatives or also adamantine.

Suitable alkoxy radicals $R^3$ are those containing from 1 to 12 carbon atoms, preferably from 1 to 8 carbon atoms. The following are given by way of example:

| | |
|---|---|
| methoxy | ethoxy |
| iso-propoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

Alkoxycarbonyl radicals $R^3$ are, for example, esters which contain the abovementioned alkoxy radicals or radicals of higher alcohols, for example, containing up to 20 carbon atoms, such as iso-$C_{15}$-alcohol.

Suitable mono- or dialkylamino radicals $R^3$ are those which contain alkyl radicals having from 1 to 12 carbon atoms, for example methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Aryl is taken to mean aromatic rings or ring systems having from 6 to 18 carbon atoms in the ring system, for example phenyl or naphthyl, which may be unsubstituted or substituted by one or more radicals such as halogen, for example fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Preference is given to unsubstituted or substituted phenyl, methoxyphenyl and naphthyl.

Heteroaryl radicals are advantageously simple or fused aromatic ring systems having one or more heteroaromatic 3- to 7-membered rings. The heteroatoms present in the ring or ring system may be one or more nitrogen, sulfur and/or oxygen atoms.

Examples of hydrophilic radicals, i.e. radicals imparting water solubility to the compounds of the formula I, $R^3$ are carboxyl and sulfoxy radicals and, in particular, salts thereof with any desired physiologically compatible cations, such as the alkali metal salts or the trialkylammonium salts, such as tri-(hydroxyalkyl) ammonium salts or the 2-methylpropan-1-ole-2-ammonium salts. Alkylammonium radicals containing any desired physiologically compatible anion are also suitable.

Preference is given to those compounds of the formula I in which the variables independently of one another have the following meanings:

$R^1$ and $R^2$ are $COOR^4$, $COR^4$, $CONR^4R^5$ or CN;

$R^3$ is hydrogen, $C_1$–$C_8$-alkyl, $C_1$–$C_8$-alkoxy, $C_1$–$C_{20}$-alkoxycarbonyl, $C_1$–$C_{12}$-alkylamino, $C_1$–$C_{12}$-dialkylamino, aryl or heteroaryl, substituted or unsubstituted, substituents which confer solubility in water, selected from the group consisting of carboxylate, sulfonate or alkylammonium radicals;

$R^4$ and $R^5$ are hydrogen, $C_1$–$C_8$-alkyl, $C_5$–$C_6$-cycloalkyl or phenyl.

Particular preference is given to those compounds of the formula I in which the variables independently of one another have the following meanings:

$R^1$ and $R^2$ are $COOR^4$, $COR^4$, $CONR^4R^5$ or CN;

$R^3$ is hydrogen, $C_1$–$C_8$-alkyl, $C_1$–$C_8$-alkoxy, $C_1$–$C_{20}$-alkoxycarbonyl, $C_1$–$C_{12}$-alkylamino, $C_1$–$C_{12}$-dialkylamino, aryl or heteroaryl, substituted or unsubstituted, or a sulfonate radical; and $R^4$ and $R^5$ are hydrogen or $C_1$–$C_8$-alkyl.

Particularly preferred alkyl radicals $R^3$ to $R^5$ which may be mentioned are branched or unbranched $C_1$–$C_8$-alkyl chains, in particular methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 2-ethyl-hexyl or n-octyl.

Particularly preferred cycloalkyl radicals $R^4$ and $R^5$ which may be mentioned are branched or unbranched $C_5$–$C_6$-cycloalkyl chains, such as cyclopentyl and cyclohexyl.

Particularly preferred alkoxy radicals $R^3$ are those containing from 1 to 8 carbon atoms, preferably from 1 to 6 carbon atoms.

The following are mentioned by way of example:

| | |
|---|---|
| methoxy | ethoxy |
| iso-propoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |

Very particular preference is given to those compounds of the formula Ia,

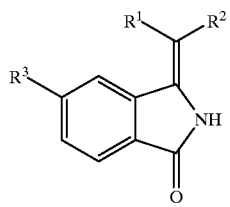

Ia in which the variables independently of one another have the following meanings:

$R^1$ and $R^2$ are $COOR^4$, $COR^4$, $CONR^4R^5$ or CN;

$R^3$ is hydrogen, $C_1$–$C_8$-alkyl, $C_1$–$C_4$-alkoxy, $C_1$–$C_8$-alkoxycarbonyl or sulfonate radical; and $R^4$ and $R^5$ are hydrogen or $C_1$–$C_8$-alkyl.

Particularly preferred suitable alkoxy radicals $R^3$ are those having from 1 to 4 carbon atoms.

The following are to be mentioned by way of example:

| | |
|---|---|
| methoxy | ethoxy |
| iso-propoxy | n-propoxy |
| 1-methylpropoxy | n-butoxy |

Alkoxycarbonyl radicals $R^3$ are esters which contain $C_1$–$C_8$-alkoxy radicals.

In particular, the following alkoxy radicals are to be mentioned:

| | |
|---|---|
| methoxy | ethoxy |
| iso-propoxy | n-propoxy |
| 1-methylpropoxy | n-butoxy |
| n-pentoxy | 2-methylpropoxy |
| 3-methylbutoxy | 1,1-dimethylpropoxy |
| 2,2-dimethylpropoxy | hexoxy |
| 1-methyl-1-ethylpropoxy | heptoxy |
| octoxy | 2-ethylhexoxy |

As regards the spatial positioning of the substituents $R^1$ and $R^2$ at the C—C double bond, the structure I covers both the respective E- and also the Z-isomers. Of course, mixtures of the two isomers are also possible.

The novel isoindolinone derivatives I are highly suitable for stabilizing organic material inter alia against the effect of light, oxygen and heat. They are added to the organic material to be stabilized in a concentration of from 0.01 to 10% by weight, preferably from 0.01 to 5% by weight, particularly preferably from 0.02 to 2% by weight, based on the organic material, before, during or after its preparation.

Organic material is to be taken to mean, for example, photographic recording material, in particular photographic emulsions, or precursors for plastics and surface coatings, but in particular plastics and surface coatings themselves.

Organic material is, however, also taken to mean cosmetic preparations, for example ointments and lotions, and also medicament preparations, for example pills and suppositories.

The present invention further relates to organic material, in particular plastics and surface coatings, stabilized against the effect of light, oxygen and heat, comprising from 0.01 to 10% by weight, preferably from 0.01 to 5% by weight, particularly preferably from 0.02 to 2% by weight, based on the amount of organic material, of one or more isoindolinone derivatives of the formula I.

The novel compounds I can be mixed especially with plastics using any known devices and methods for mixing stabilizing agents or other additives into polymers.

The organic material stabilized by the novel compounds I may, if desired, comprise other additives, for example antioxidants, light stabilizing agents, metal deactivators, antistatic agents, flame retardants, pigments and fillers.

Antioxidants and light stabilizers which may be added in addition to the novel compounds are, for example, compounds based on sterically hindered phenols or costabilizers containing sulfur or phosphorus.

Examples of such phenolic antioxidants which may be mentioned are 2,6-di-tert-butyl-4-methylphenol, n-octadecyl-β-(3,5-di-tert-butyl-4-hydroxyphenyl) propionate, 1,1,3-tris (2-methyl-4-hydroxy-5-tert-butylphenyl)butane, 1,3,5-trimethyl-2,4,6-tris(3,5-di-tert-butyl-4-hydroxy-benzyl)benzene, 1,3,5-tris(3,5-di-tert-butyl-4-hydroxybenzyl) isocyanurate, 1,3,5-tris[β-(3,5-di-tert-butyl-4-hydroxyphenyl)propionylethyl] isocyanurate, 1,3,5-tris-(2,6-dimethyl-3-hydroxy-4-tert-butylbenzyl) isocyanurate and pentaerythritol tetrakis [β-(3,5-di-tert-butyl-4-hydroxyphenyl)propionate].

Examples of suitable phosphorus-containing antioxidants are tris(nonylphenyl) phosphite, distearylpentaerythritol diphosphite, tris(2,4-di-tert-butylphenyl) phosphite, tris(2-tert-butyl-4-methylphenyl) phosphite, bis(2,4-di-tert-butylphenyl)pentaerythritol diphosphite and tetrakis(2,4-di-tert-butylphenyl) 4,4'-biphenylenediphosphite.

Examples of antioxidants containing sulfur are dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Other antioxidants and light stabilizers which may be used together with the compounds I are, for example, 2-(2'-hydroxyphenyl)benzotriazoles, 2-hydroxybenzophenones, aryl esters of hydroxybenzoic acids, α-cyanocinnamic acid derivatives, benzimidazolecarboxanilides, nickel compounds or oxalanilides.

Particularly good stabilization is achieved when at least one light stabilizer from the compound class of sterically hindered amines is also added in the usual concentration to the compounds I.

Examples of suitable sterically hindered amines are: bis (2,2,6,6-tetramethylpiperidyl) sebacate, bis(1,2,2,6,6-pentamethylpiperidyl) sebacate, the condensation product of 1-hydroxyethyl-2,2,6,6-tetramethyl-4-hydroxypiperidine and succinic acid, the condensation product of N,N'-di(2,2,6,6-tetramethylpiperidyl)hexamethylenediamine and 4-tert-octylamino-2,6-dichloro-1,3,5-triazine, tris(2,2,6,6-tetramethylpiperidyl) nitrilotriacetate, tetrakis(2,2,6,6-tetramethyl-4-piperidyl) 1,2,3,4-butane-tetracarboxylate, 1,1'-(1,2-ethanediyl)-bis(3,3,5,5-tetramethylpiperazinone), the condensation products of 4-amino-2,2,6,6-tetramethylpiperidines and tetramethylolacetylenediureas.

Examples which may be mentioned of plastics which may be stabilized by the novel compounds I are:

polymers of mono- and diolefins, for example low density or high density polyethylene, polypropylene, linear poly-1-butene, polyisoprene, polybutadiene and copolymers of mono- or diolefins or mixtures of said polymers;

copolymers of mono- or diolefins with other vinyl monomers, for example ethylene-alkyl acrylate copolymers, ethylene-alkyl methacrylate copolymers, ethylene-vinyl acetate copolymers or ethylene-acrylic acid copolymers;

polystyrene and copolymers of styrene or α-methylstyrene with dienes and/or acryl derivatives, for example styrene-butadiene, styrene-acrylonitrile (SAN), styrene-ethyl methacrylate, styrene-butadiene-ethyl acrylate, styrene-acrylonitrile methacrylate, acrylonitrile-butadiene-styrene (ABS) or methyl methacrylate-butadiene-styrene (MBS);

halogen-containing polymers, for example polyvinyl chloride, polyvinyl fluoride, polyvinylidene fluoride and copolymers thereof;

polymers derived from α,β-unsaturated acids and derivatives thereof, such as polyacrylates, polymethacrylates, polyacrylamides and polyacrylonitriles;

polymers derived from unsaturated alcohols and amines or acyl derivatives or acetals thereof, for example polyvinyl alcohol and polyvinyl acetate;

polyurethanes, polyamides, polyureas, polyesters, polycarbonates, polysulfonates, polyether sulfones and polyether ketones.

Furthermore, the novel compounds I can be used to stabilize surface coatings, for example industrial finishes. Of these, particular attention is drawn to baking finishes, and, in turn, of these, automotive finishes, preferably two-coat finishes.

Compounds I can be added to the surface coating in solid or dissolved form. Their good solubility in the surface coating systems is thus of particular advantage.

Even when the compounds are used as stabilizers in surface coatings, it is possible also to use the additional additives already listed, in particular antioxidants and light stabilizers.

The novel compounds I are notable for good compatibility with customary types of plastics and good solubility in customary surface coating systems and in customary cosmetic oils. They are generally colorless or have only a slight intrinsic color, are stable and nonvolatile at the customary processing temperatures for plastics and surface coatings, show only a slight tendency to migrate and, above all, effect a long period of protection in the organic materials treated therewith.

Furthermore, the novel isoindolinone derivatives I are also suitable as photostable UV filters in cosmetic and pharmaceutical preparations for protecting human skin or human hair from solar radiation but also against artificial light which has a high UV content, alone or together with compounds known for cosmetic or pharmaceutical preparations which absorb in the UV region. Organic materials are therefore taken in the widest sense also to include human skin and human hair. The cosmetic and pharmaceutical preparations as such are of course also stabilized at the same time in order to remain effective for as long as possible.

Accordingly, the present invention also relates to cosmetic and pharmaceutical preparations for protecting human skin or human hair against UV light in the region from 280 to 400 nm, which comprise from 0.01 to 10% by weight, preferably from 0.1 to 8% by weight, particularly preferably from 2 to 7% by weight, based on the amount of cosmetic or pharmaceutical preparation, of one or more isoindolinone derivatives I alone or together with compounds known for cosmetic or pharmaceutical preparations which absorb in the UV region as light protection agents.

The cosmetic and pharmaceutical preparations comprising light protection agents are normally based on a carrier which comprises at least an oil phase. Preparations based solely on aqueous components are, however, also possible if compounds containing hydrophilic substituents are used. Accordingly, suitable preparations are oils, oil-in-water and water-in-oil emulsions, creams and pastes, lip-protection stick compositions or fat-free gels.

Such sunscreen preparations can accordingly be in liquid, pasty or solid form, for example as water-in-oil creams, oil-in-water creams and lotions, aerosol foam creams, gels, oils, marking pencils, powders, sprays or alcoholic/aqueous lotions.

Examples of conventional oil components in cosmetics are liquid paraffin, glyceryl stearate, isopropyl myristate, diisopropyl adipate, acetylstearyl 2-ethylhexanoate, hydrogenated polyisobutene, vaseline, caprylic acid/capric acid triglycerides, microcrystalline wax, lanolin and stearic acid.

Examples of conventional cosmetic auxiliaries which may be suitable as additives are coemulsifiers, fats and waxes, stabilizers, thickeners, biogenic active ingredients, film formers, fragrances, dyes, pearlizing agents, preservatives, pigments, electrolytes (e.g. magnesium sulfate) and pH regulators. Suitable coemulsifiers are, preferably, known W/O and also O/W emulsifiers, such as polyglycerol esters, sorbitan esters or partially esterified glycerides. Typical examples of fats are glycerides; waxes which may be mentioned include beeswax, paraffin wax or microwaxes, if desired in combination with hydrophilic waxes. Stabilizers which may be used are metal salts of fatty acids, for example magnesium stearate, aluminum stearate and/or zinc stearate. Examples of suitable thickeners are crosslinked polyacrylic acids and derivatives thereof, polysaccharides, in particular xanthan gum, guar guar, agar agar, alginates and tyloses, carboxymethylcellulose and hydroxyethylcellulose, also fatty alcohols, monoglycerides and fatty acids, polyacrylates, polyvinyl alcohol and polyvinyl pyrrolidone. Biogenic active ingredients are taken to mean, for example, plant extracts, protein hydrolysates and vitamin complexes. Examples of traditional film formers are hydrocolloids such as chitosan, microcrystalline chitosan or quaternized chitosan, polyvinylpyrrolidone, vinylpyrrolidone-vinyl acetate copolymers, polymers of the acrylic acid series, quaternary cellulose derivatives and similar compounds. Suitable preservatives are, for example, formaldehyde solution, p-hydroxybenzoate or sorbic acid. Suitable pearlizing agents are, for example, glycol distearic esters, such as ethylene glycol distearate, but also fatty acids and fatty acid monoglycol esters. The dyes which may be used are those substances suitable and approved for cosmetic purposes, such as, for example, those listed in the publication Kosmetische Färbemittel from the Farbstoffkommission der Deutschen Forschungsgemeinschaft, published by Verlag Chemie, Weinheim, 1984. These dyes are normally used in concentrations of from 0.001 to 0.1% by weight, based on the total mixture.

The total amount of auxiliaries and additives can be from 1 to 80% by weight, preferably from 6 to 40% by weight, and the nonaqueous content ("active substance") can be from 20 to 80% by weight, preferably from 30 to 70% by weight, based on the formulation. The formulations can be prepared in a manner known per se, i.e. for example by hot, cold, hot/cold and PIT emulsification. This is purely a mechanical process and there is no chemical reaction.

Finally, it is possible additionally to use further substances known per se which absorb in the UV region, provided they are photostable in the overall system of the preparation to be used according to the invention.

UV filter substances which are used in combination with the compounds of the formula I to be used according to the invention are any UV-A and UV-B filter substances. Examples which may be mentioned are:

TABLE 1

| No. | Substance | CAS No. (= acid) |
|---|---|---|
| 1 | 4-Aminobenzoic acid | 150-13-0 |
| 2 | 3-(4'-Trimethylammonio)benzylidene-2-bornanone methylsulfate | 52793-97-2 |
| 3 | 3,3,5-Trimethylcyclohexyl salicylate (homosalate) | 118-56-9 |
| 4 | 2-Hydroxy-4-methoxybenzophenone (oxybenzone) | 131-57-7 |
| 5 | 2-Phenylbenzimidazole-5-sulfonic acid and its potassium, sodium and triethanolamine salts | 27503-81-7 |
| 6 | 3,3'-(1,4-Phenylenedimethine)bis(7,7-di-methyl-2-oxobicyclo[2.2.1]heptane-1-methane-sulfonic acid) and its salts | 90457-82-2 |
| 7 | Polyethoxyethyl 4-bis(polyethoxy)aminobenzoate | 113010-52-9 |
| 8 | 2-Ethylhexyl 4-dimethylaminobenzoate | 21245-02-3 |
| 9 | 2-Ethylhexyl salicylate | 118-60-5 |
| 10 | Isoamyl 4-methoxycinnamate | 71617-10-2 |
| 11 | 2-Ethylhexyl 4-methoxycinnamate | 5466-77-3 |
| 12 | 2-Hydroxy-4-methoxybenzophenone-5-sulfonic acid (sulisobenzone) and the sodium salt | 4065-45-6 |
| 13 | 3-(4'-Methylbenzylidene)-2-bornanone | 36861-47-9 |
| 14 | 3-Benzylidene-2-bornanone | 15087-24-8 |
| 15 | 1-(4'-Isopropylphenyl)-3-phenyl-1,3-propanedione | 63250-25-9 |
| 16 | 4-Isopropylbenzyl salicylate | 94134-93-7 |
| 17 | 2,4,6-Tris (o-2-ethylhexoxycarbonyl-anilino)-1,3,5-triazine | 88122-99-0 |
| 18 | 3-(4-Imidazolyl)acrylic acid and its ethyl ester | 104-98-3 |
| 19 | Ethyl 2-cyano-3,3-diphenylacrylate | 5232-99-5 |
| 20 | 2'-Ethylhexyl 2-cyano-3,3-diphenylacrylate | 6197-30-4 |
| 21 | Menthyl o-aminobenzoate or 5-menthyl 2-aminobenzoate | 134-09-8 |
| 22 | Glyceryl p-aminobenzoate or 1-glyceryl 4-aminobenzoate | 136-44-7 |
| 23 | 2,2'-Dihydroxy-4-methoxybenzophenone (dioxybenzone) | 131-53-3 |
| 24 | 2-Hydroxy-4-methoxy-4-methylbenzophenone (mexenone) | 1641-17-4 |
| 25 | Triethanolamine salicylate | 2174-16-5 |
| 26 | Dimethoxyphenylglyoxalic acid or sodium 3,4-dimethoxyphenylglyoxalate | 4732-70-1 |
| 27 | 3-(4'-Sulfobenzylidene)-2-bornanone and its salts | 56039-58-8 |
| 28 | 4-tert-Butyl-4'-methoxydibenzoylmethane | 70356-09-1 |
| 29 | 2,2',4,4'-Tetrahydroxybenzophenone | 131-55-5 |

To protect human hair against UV rays, the novel light protection agents of the formula I can be incorporated into shampoos, lotions, gels, hairsprays, aerosol foam creams or emulsions in concentrations of from 0.01 to 10% by weight, preferably from 0.1 to 8% by weight, particularly preferably from 2 to 7% by weight. The corresponding formulations can be used inter alia for washing, coloring and styling the hair.

The compounds to be used according to the invention are generally notable for particularly high absorbance in the UV-A radiation region with a sharp band structure.

Moreover, they are readily soluble in cosmetic oils and can be easily incorporated into cosmetic formulations. The emulsions prepared using the compounds I are particularly notable for their high stability, the compounds I themselves for their high photostability, and the preparations prepared using I by their pleasant feel on the skin.

The invention also relates to the compounds of the formula I for use as a medicament and also pharmaceutical preparations for the preventative treatment of inflammation and allergies of the skin and also for preventing certain types of skin cancer, these preparations comprising an effective amount of at least one compound of the formula I as active ingredient.

The novel pharmaceutical formulation can be administered orally or topically. For oral administration the pharmaceutical formulation is in the form of inter alia pastilles, gelatine capsules, sugar-coated tablets, or is a syrup, solution, emulsion or suspension. Examples of topical application forms of the pharmaceutical formulation are ointments, creams, gels, sprays, solutions or lotions.

The compounds of the formula I to be used according to the invention can be prepared, according to Chem. Ber. 1967, 2261–2273, according to the following reaction equation

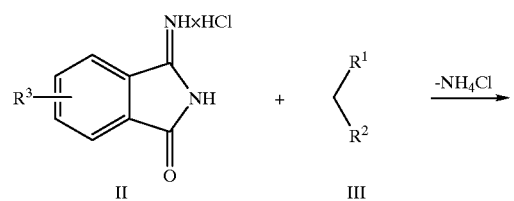

by condensing iminoisoindolinone hydrochloride of the formula II with CH-acidic compounds of the formula III, the substituents $R^1$ to $R^3$ being as defined in claim 1.

For example, the reaction of iminoisoindolinone hydrochloride with 2-ethylhexyl cyanoacetate gives compound 1 in Tab. 2.

The examples below illustrate in more detail the preparation and use of the novel isoindolinone derivatives.

I. PREPARATION

Example 1

Preparation Procedure for Compound No. 1 in Table 2

0.1 mol of iminoisoindolinone hydrochloride and 0.1 mol of 2-ethylhexyl cyanoacetate were dissolved in 50 ml of isobutanol and refluxed for 5 h. After the solvent had been removed under reduced pressure, the residue was taken up in water and crystallized to give 20 g (60% yield) of compound 1 from Table 2.

Compounds 2 to 5 listed in Table 2 were prepared as in Example 1.

TABLE 2

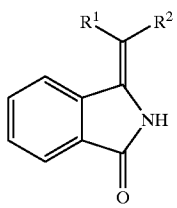

| No. | $R^1$ | $R^2$ | λmax (nm) | $E^1_1$ |
|---|---|---|---|---|
| 1) | CN | COOC$_8$H$_{17}$*) | 342, 300 | 532, 500 |
| 2) | CN | COOCH$_3$ | 342, 300 | 614, 500 |
| 3) | CN | CN | 380 | 1300 |
| 4) | CN | COC$_4$H$_9$**) | 372 | 1207 |
| 5) | CN | CONH$_2$ | 335, 300 | 600, 500 |

*) 2-ethylhexyl
**) tert-butyl

II. PREPARATIONS

General Procedure for Preparing Emulsions for Cosmetic Purposes

All oil-soluble constituents are heated to 85° C. in a stirred reactor. When all the constituents are molten, or in the form of a liquid phase, the water phase is incorporated with homogenization. With stirring, the emulsion is cooled to about 40° C., perfumed, homogenized and then cooled to 25° C. with continuous stirring.

Example 2

| Composition for lipcare | |
|---|---|
| Mass content % by weight | |
| ad 100 | Eucerinum anhydricum |
| 10.00 | Glycerol |
| 10.00 | Titanium dioxide |
| 5.00 | Compound No. 1 in Table 2 |
| 8.00 | Octyl methoxycinnamate |
| 5.00 | Zinc oxide |
| 4.00 | Castor oil |
| 4.00 | Pentaerythrithyl stearate/caprate/caprylate/adipate |
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

Example 3

| Composition for lipcare | |
|---|---|
| Mass content % by weight | |
| ad 100 | Eucerinum anhydricum |
| 10.00 | Glycerol |
| 10.00 | Titanium dioxide |
| 5.00 | Compound No. 2 in Table 2 |
| 8.00 | Octyl methoxycinnamate |
| 5.00 | Zinc oxide |
| 4.00 | Castor oil |
| 4.00 | Pentaerythrithyl stearate/caprate/caprylate/adipate |

Composition for lipcare

| Mass content % by weight | |
|---|---|
| 3.00 | Glyceryl stearate SE |
| 2.00 | Beeswax |
| 2.00 | Microcrystalline wax |
| 2.00 | Quaternium-18 bentonite |
| 1.50 | PEG-45/dodecyl glycol copolymer |

Example 4

Composition for sunblock with micropigments

| Mass content % by weight | |
|---|---|
| ad 100 | Water |
| 10.00 | Octyl methoxycinnamate |
| 6.00 | PEG-7-hydrogenated castor oil |
| 6.00 | Titanium dioxide |
| 5.00 | Compound No. 1 in Table 2 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40-hydrogenated castor oil |
| 0.50 | Tocopheryl acetate |
| 0.50 | Phenoxyethanol |
| 0.20 | EDTA |

Example 5

Composition for sunblock with micropigments

| Mass content % by weight | |
|---|---|
| ad 100 | Water |
| 10.00 | Octyl methoxycinnamate |
| 6.00 | PEG-7-hydrogenated castor oil |
| 6.00 | Titanium dioxide |
| 5.00 | Compound No. 2 in Table 2 |
| 5.00 | Mineral oil |
| 5.00 | Isoamyl p-methoxycinnamate |
| 5.00 | Propylene glycol |
| 3.00 | Jojoba oil |
| 3.00 | 4-Methylbenzylidenecamphor |
| 2.00 | PEG-45/dodecyl glycol copolymer |
| 1.00 | Dimethicone |
| 0.50 | PEG-40-hydrogenated castor oil |
| 0.50 | Tocopheryl acetate |
| 0.50 | Phenoxyethanol |
| 0.20 | EDTA |

Example 6

Fat-free gel

| Mass content % by weight | |
|---|---|
| ad 100 | Water |
| 8.00 | Octyl methoxycinnamate |
| 7.00 | Titanium dioxide |
| 5.00 | Compound No. 1 in Table 2 |
| 5.00 | Glycerol |
| 5.00 | PEG-25 PABA |
| 1.00 | 4-Methylbenzylidenecamphor |
| 0.40 | Acrylate C10-C30 alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 7

Fat-free gel

| Mass content % by weight | |
|---|---|
| ad 100 | Water |
| 8.00 | Octyl methoxycinnamate |
| 7.00 | Titanium dioxide |
| 5.00 | Compound No. 2 in Table 2 |
| 5.00 | Glycerol |
| 5.00 | PEG-25 PABA |
| 1.00 | 4-Methylbenzylidenecamphor |
| 0.40 | Acrylate C10-C30 alkyl acrylate crosspolymer |
| 0.30 | Imidazolidinylurea |
| 0.25 | Hydroxyethylcellulose |
| 0.25 | Sodium methylparaben |
| 0.20 | Disodium EDTA |
| 0.15 | Fragrance |
| 0.15 | Sodium propylparaben |
| 0.10 | Sodium hydroxide |

Example 8

Sun cream (SPF 20)

| Mass content % by weight | |
|---|---|
| ad 100 | Water |
| 8.00 | Octyl methoxycinnamate |
| 8.00 | Titanium dioxide |
| 6.00 | PEG-7-hydrogenated castor oil |
| 5.00 | Compound No. 1 in Table 2 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |

-continued

Sun cream (SPF 20)

| Mass content % by weight | |
|---|---|
| 0.20 | Disodium EDTA |
| 0.15 | Propylparaben |

Example 9

Sun cream (SPF 20)

| Mass content % by weight | |
|---|---|
| ad 100 | Water |
| 8.00 | Octyl methoxycinnamate |
| 8.00 | Titanium dioxide |
| 6.00 | PEG-7-hydrogenated castor oil |
| 5.00 | Compound No. 2 in Table 2 |
| 6.00 | Mineral oil |
| 5.00 | Zinc oxide |
| 5.00 | Isopropyl palmitate |
| 5.00 | Imidazolidinylurea |
| 3.00 | Jojoba oil |
| 2.00 | PEG-45/dodecyl glycol copolymer |
| 1.00 | 4-Methylbenzylidenecamphor |
| 0.60 | Magnesium stearate |
| 0.50 | Tocopheryl acetate |
| 0.25 | Methylparaben |
| 0.20 | Disodium EDTA |
| 0.15 | Propylparaben |

Example 10

Sun cream, water-resistant

| Mass content % by weight | |
|---|---|
| ad 100 | Water |
| 8.00 | Octyl methoxycinnamate |
| 5.00 | PEG-7-hydrogenated castor oil |
| 5.00 | Propylene glycol |
| 4.00 | Isopropyl palmitate |
| 4.00 | Caprylic/capric triglyceride |
| 5.00 | Compound No. 1 in Table 2 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 11

Sun cream, water-resistant

| Mass content % by weight | |
|---|---|
| ad 100 | Water |
| 8.00 | Octyl methoxycinnamate |
| 5.00 | PEG-7-hydrogenated castor oil |
| 5.00 | Propylene glycol |
| 4.00 | Isopropyl palmitate |
| 4.00 | Caprylic/capric triglyceride |
| 5.00 | Compound No. 2 in Table 2 |
| 4.00 | Glycerol |
| 3.00 | Jojoba oil |
| 2.00 | 4-Methylbenzylidenecamphor |
| 2.00 | Titanium dioxide |
| 1.50 | PEG-45/dodecyl glycol copolymer |
| 1.50 | Dimethicone |
| 0.70 | Magnesium sulfate |
| 0.50 | Magnesium stearate |
| 0.15 | Fragrance |

Example 12

Sun milk (SPF 6)

| Mass content % by weight | |
|---|---|
| ad 100 | Water |
| 10.00 | Mineral oil |
| 6.00 | PEG-7-hydrogenated castor oil |
| 5.00 | Isopropyl palmitate |
| 3.50 | Octyl methoxycinnamate |
| 5.00 | Compound No. 1 in Table 2 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |
| 0.15 | Propylparaben |
| 0.05 | Tocopherol |

Example 13

Sun milk (SPF 6)

| Mass content % by weight | |
|---|---|
| ad 100 | Water |
| 10.00 | Mineral oil |
| 6.00 | PEG-7-hydrogenated castor oil |
| 5.00 | Isopropyl palmitate |
| 3.50 | Octyl methoxycinnamate |
| 5.00 | Compound No. 2 in Table 2 |
| 3.00 | Caprylic/capric triglyceride |
| 3.00 | Jojoba oil |
| 2.00 | PEG-45/dodecyl glycol copolymer |
| 0.70 | Magnesium sulfate |
| 0.60 | Magnesium stearate |
| 0.50 | Tocopheryl acetate |
| 0.30 | Glycerol |
| 0.25 | Methylparaben |

-continued

Sun milk (SPF 6)

| Mass content % by weight | |
|---|---|
| 0.15 | Propylparaben |
| 0.05 | Tocopherol |

Example 14

Stabilization of Polystyrene

To assess the stabilizer effect of the UV absorbers, the latter were incorporated into polystyrene 168 N (BASF) in a concentration of 0.2% by weight. To this end, the polystyrene and the stabilizer were premixed and dissolved and granulated via a single-neck extruder at a composition temperature of 200° C. Test pieces (60×45×2 mm) were prepared from the resulting granular product using an injection molding machine at 200° C. The test pieces were artificially weathered in a Xenotest® 1200 accelerated weathering apparatus (Hanau) for up to 1000 hours. The yellowness index (YI) of the samples was determined according to the Annual Book of ASTM Standards D 1925-70 (Reapproved 1977) as a measure of the degree of yellowing. The results are given in Table 3.

TABLE 3

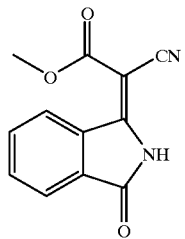

YI values of polystyrene

| | YI values Exposure time | |
|---|---|---|
| | 500 h | 1000 h |
| Stabilized with compound 2 from Table 2 | 10 | 18 |
| Comparative experiment without stabilizer | >50 | |

We claim:

1. A cosmetic or pharmaceutical preparation for protecting human skin or human hair from solar radiation or artificial light which has a high UV content, comprising at least one isoindolinone compound of the formula I,

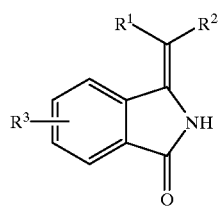

I in which the variables independently of one another have the following meanings:

$R^1$ and $R^2$ are $COOR^4$, $COR^4$, $CONR^4R^5$ or CN;

$R^3$ is hydrogen, $C_1$–$C_8$-alkyl, $C_1$–$C_8$-alkoxy, $C_1$–$C_{20}$-alkoxycarbonyl, $C_1$–$C_{12}$-alkylamino, $C_1$–$C_{12}$-dialkylamino, aryl or heteroaryl, substituted or unsubstituted, substituents which confer solubility in water, selected from the group consisting of carboxylate, sulfonate and alkylammonium radicals;

$R^4$ and $R^5$ are hydrogen, $C_1$–$C_8$-alkyl, $C_5$–$C_6$-cycloalkyl or phenyl, as photostable UV filter.

2. The preparation of claim 1, wherein the variables of the compound I independently of one another are as follows:

$R^1$ and $R^2$ are $COOR^4$, $COR^4$, $CONR^4R^5$ or CN;

$R^3$ is hydrogen, $C_1$–$C_8$-alkyl, $C_1$–$C_8$-alkoxy, $C_1$–$C_{20}$-alkoxycarbonyl, $C_1$–$C_{12}$-alkylamino, $C_1$–C12-dialkylamino, aryl or heteroaryl, substituted or unsubstituted, or a sulfonate radical; and $R^4$ and $R^5$ are hydrogen or $C_1$–$C_8$-alkyl.

3. The preparation of claim 1, wherein said at least one compound of formula I is present in an amount of from 0.01 to 10% by weight of the total preparation.

4. A process of protecting human skin or human hair from solar radiation comprising applying to said skin or hair the composition of claim 1.

* * * * *

UNITED STATES PATENT AND TRADEMARK OFFICE
CERTIFICATE OF CORRECTION

PATENT NO. : 6,210,657 B1
DATED : April 3, 2001
INVENTOR(S) : Habeck et al.

Page 1 of 1

It is certified that error appears in the above-identified patent and that said Letters Patent is hereby corrected as shown below:

<u>Column 16, claim 2,</u>
Line 41, "$C_1$-C12-" should be -- $C_1$-$C_{12}$- --.

Signed and Sealed this

Twenty-fifth Day of September, 2001

Attest:

NICHOLAS P. GODICI
Attesting Officer
*Acting Director of the United States Patent and Trademark Office*